United States Patent [19]
Nakamori et al.

[11] Patent Number: 5,565,213
[45] Date of Patent: Oct. 15, 1996

[54] STABLE LIPOSOME AQUEOUS SUSPENSION

[75] Inventors: Katsu Nakamori; Tsuguchika Yoshida; Ikuo Koyama; Toshiaki Nakajima; Mikiko Odawara, all of Saitama, Japan

[73] Assignee: Taisho Pharmaceutical Co., Ltd., Tokyo, Japan

[21] Appl. No.: 318,750

[22] PCT Filed: Apr. 21, 1992

[86] PCT No.: PCT/JP92/00512
§ 371 Date: Oct. 21, 1994
§ 102(e) Date: Oct. 21, 1994

[87] PCT Pub. No.: WO93/20934
PCT Pub. Date: Oct. 28, 1993

[51] Int. Cl.$^6$ .................................................. A61K 9/127
[52] U.S. Cl. .................................... 424/450; 428/402.2
[58] Field of Search .................... 424/450; 428/402.2

[56] References Cited

U.S. PATENT DOCUMENTS

| | | | |
|---|---|---|---|
| 4,818,537 | 4/1989 | Guo | 424/427 |
| 5,228,446 | 7/1993 | Unger | 128/662.02 |

FOREIGN PATENT DOCUMENTS

| | | |
|---|---|---|
| 62-42733 | 2/1987 | Japan . |
| 2-501730 | 6/1990 | Japan . |
| 3-74323 | 3/1991 | Japan . |
| 5212269 | 8/1993 | Japan . |
| 88/03018 | 5/1988 | WIPO . |

*Primary Examiner*—Gollamudi S. Kishore
*Attorney, Agent, or Firm*—Oblon, Spivak, McClelland, Maier & Neustadt, P.C.

[57] ABSTRACT

A liposome aqueous suspension containing taurine and benzalkonium chloride is disclosed. The liposome aqueous suspension undergoes no precipitation, agglomeration or change in particle size even when preserved at 40° C. for 6 months and is inhibited from lyso-phospholipid formation.

1 Claim, No Drawings

STABLE LIPOSOME AQUEOUS SUSPENSION

TECHNICAL FIELD

This invention relates to an aqueous suspension of liposomes which can be preserved stably.

BACKGROUND ART

Liposomes are closed vesicles comprising a lipid bilayer. Taking advantage of bioaffinity of liposomes, a number of proposals have been made to incorporate various drugs into the inner aqueous phase or the lipid bilayer of liposomes for use as a drug carrier. In many cases, however, liposomes as suspended in water are colloid-chemically instable, tending to undergo agglomeration or fusion among themselves, precipitation due to crystallization of the membrane component, an increase in particle size, or hydrolysis to form lyso-phospholipids that are considered to be hemolytic. These changes in effect and appearance result in impairment of commercial values.

Unexamined Published Japanese Patent Application No. 42733/87 furnishes a solution for the problem, which comprises stabilizing liposomes using an amino acid. What is achieved by this technique is stabilization in preservation at room temperature or lower temperatures, and stabilization in high temperature preservation was still insufficient. The technique was also insufficient for inhibition of lyso-phospholipid formation.

An object of the present invention is to provide a stable liposome aqueous suspension which does not undergo precipitation, agglomeration or change in particle size even when preserved at 40° C. for 6 months and in which lyso-phospholipid formation is suppressed.

DISCLOSURE OF THE INVENTION

The present invention provides a liposome aqueous suspension containing taurine and benzalkonium chloride.

Taurine is added in an amount of from 0.5 to 5.0% by weight, preferably from 1.0 to 3.0% by weight, based on the total amount of the liposome preparation, which amount corresponds to a molar ratio of from 1:13 to 1:133, preferably from 1:27 to 1:80, to the membrane component of the liposomes. Benzalkonium chloride is added in an amount of from 0.05 to 20 mol %, preferably from 2 to 8 mol %, based on the membrane component of the liposomes.

While not limiting, the liposome aqueous suspension of the present invention can be prepared as follows. A membrane component hereinafter described is dissolved in an organic solvent, and the organic solvent is evaporated. The residual lipid membrane is then subjected to (A) hydration with an aqueous solution containing taurine and benzalkonium chloride or (B) hydration with a taurine aqueous solution followed by addition of benzalkonium chloride.

The membrane component which can be used in the present invention includes hydrogenated soybean lecithin, hydrogenated egg yolk lecithin, dimyristoylphosphatidylcholine, dipalmitoylphosphatidylcholine, and distearoylphosphatidylcholine. A membrane stabilizer, such as cholesterol, may be added to the system, while not essential. The amount of the membrane component to be used ranges usually from 0.0005 to 0.025 part by weight, and preferably from 0.001 to 0.008 part by weight, per part by weight of water.

The organic solvent to be used includes chloroform and dichloromethane.

It is preferable to adjust the liposome aqueous suspension to a pH around neutrality (i.e., pH 6.0 to 7.0) with sodium hydroxide, potassium hydroxide, etc.

If desired, the size of liposome may be controlled by means of a polycarbonate-made membrane filter or a high-pressure jet type homogenizer.

If desired, the liposome aqueous suspension of the present invention may further contain additives as long as the effects of the present invention are not impaired. Useful additives include antiseptics (e.g., methyl p-hydroxybenzoate, ethyl p-hydroxybenzoate, and propyl p-hydroxybenzoate), antihistaminics (e.g., diphenhydramine hydrochloride, isothipendyl hydrochloride, and chlorpheniramine maleate), vitamins (e.g., vitamin A or esters thereof, activated vitamin $B_2$, vitamin $B_6$, vitamin $B_{12}$, and vitamin E and esters thereof), topical anesthetics (e.g., lidocaine, lidocaine hydrochloride, procaine hydrochloride, and dibucaine hydrochloride), refreshers (e.g., l-menthol, borneol, camphor and mentha oil), polymeric additives (e.g., polyethylene glycol, polyvinyl alcohol, polyvinyl pyrrolidone, hydroxyethyl cellulose, and hydroxypropylmethyl cellulose), isotonic agents (e.g., sodium chloride and potassium chloride), and the like.

The drug which can be retained in the liposomes is not particularly limited. For example, a water-soluble drug is dissolved in an aqueous solution of taurine (and benzalkonium chloride), added to the lipid membrane, and hydrated. An oil-soluble drug is dissolved in a solvent, such as chloroform, together with the membrane component and, after evaporation of the solvent, hydrated with an aqueous solution containing taurine (and benzalkonium chloride).

BEST MODE FOR CARRYING OUT THE INVENTION

The present invention will now be illustrated in greater detail with reference to Examples and Test Examples.

EXAMPLE 1

In an Erlenmeyer flask were placed 200 mg of dimyristoylphosphatidylcholine and 50 m of vitamin E acetate as a fat-soluble drug and dissolved in 50 ml of chloroform. Chloroform was thoroughly evaporated, and to the residue was added 10 ml of a 3% taurine aqueous solution adjusted to pH 6.5 with sodium hydroxide. After hydration at 40° to 50° C., the reaction mixture was subjected to sizing by filtering twice through a polycarbonate membrane filter having a pore size of 0.2 μm under pressure. A 5 ml aliquot of the resulting suspension was added to benzalkonium chloride to a final concentration of 0.005 w/v %, which corresponded to about 5 mol % based on the membrane component, and a 3% taurine aqueous solution at pH 6.5 was further added thereto to make 50 ml.

EXAMPLE 2

A liposome aqueous suspension was prepared in the same manner as in Example 1, except for replacing 200 mg of dimyristoylphosphatidylcholine as the membrane component with 200 mg of dipalmitoylphosphatidylcholine.

EXAMPLE 3

A liposome aqueous suspension was prepared in the same manner as in Example 1, except for replacing 200 mg of dimyristoylphosphatidylcholine as the membrane component with 200 mg of hydrogenated soybean lecithin and conducting hydration and sizing at 60° to 70° C.

EXAMPLE 4

A liposome aqueous suspension was prepared in the same manner as in Example 3, except for replacing 200 mg of hydrogenated soybean lecithin with 200 mg of hydrogenated egg yolk lecithin.

EXAMPLE 5

A liposome aqueous suspension was prepared in the same manner as in Example 3, except for replacing 200 mg of hydrogenated soybean lecithin as the membrane component with 200 mg of hydrogenated soybean lecithin and 50 mg of cholesterol.

COMPARATIVE EXAMPLE 1

A liposome aqueous suspension was prepared in the same manner as in Example 1, except for replacing the taurine aqueous solution with a 13 mM phosphoric acid aqueous solution and a 140 mM sodium chloride aqueous solution.

COMPARATIVE EXAMPLE 2

A liposome aqueous suspension was prepared in the same manner as in Example 1, except for using no benzalkonium chloride.

TEST EXAMPLE 1

Each of the liposome aqueous suspensions prepared in Example 1 and Comparative Examples 1 and 2 was preserved in a 2 ml-volume transparent ampule at 40° C. or 65° C. The phosphatidylcholine was separated with time by thin layer chromatography. The spot of phosphatidylcholine was scraped off, and its phosphorus content was determined by the method of E. Gerlach and D. Deutiche (*Biochemiche Zeitschrift*, Vol. 337, p. 477 (1963)) to obtain a phosphatidylcholine content. The results obtained are shown in Table 1 below. It is seen from Table 1 that formation of lysophosphatidylcolines, the main decomposition products of a phosphatidylcholine, is suppressed in Example 1 as compared with Comparative Examples 1 and 2.

TABLE 1

| Example No. | Phosphatidylcholine Content (%) | | | | |
|---|---|---|---|---|---|
| | Initial | 65° C. × 5 Days | 65° C. × 20 Days | 65° C. × 40 Days | 40° C. × 140 Days |
| Example 1 | 100 | 100.0 | 83.6 | 72.9 | 94.5 |
| Comparative Example 1 | 100 | 98.9 | 70.0 | 55.4 | 80.1 |
| Comparative Example 2 | 100 | 97.0 | 75.4 | 60.0 | 84.0 |

TEST EXAMPLE 2

Each of the liposome aqueous suspensions of Example 1 and Comparative Examples 1 and 2 was preserved in an ampule at 40° C., and changes in appearance was observed, and the particle size was measured with time. The results obtained are shown in Table 2 below. The liposome aqueous suspension of Example 1 showed no agglomeration or precipitation of liposomes with no change in particle size, whereas the suspensions of Comparative Examples 1 and 2 suffered noticeable agglomeration and precipitation and showed an increase in particle size.

TABLE 2

| Example No. | Appearance | | | | | Particle Size (nm) | | | | |
|---|---|---|---|---|---|---|---|---|---|---|
| | Initial | 1 Mth | 2 Mth | 3 Mth | 6 Mth | Initial | 1 Mth | 2 Mth | 3 Mth | 6 Mth |
| Example 1 | − | − | − | − | − | 231 | 231 | 230 | 206 | 226 |
| Compara. Example 1 | − | − | + | + | + | 240 | 251 | 450 | 781 | 2190 |
| Compara. Example 2 | − | + | + | + | + | 250 | 285 | 331 | 445 | 1231 |

Note:
−: Neither agglomeration nor precipitation was observed.
+: Agglomeration or precipitation was observed.

INDUSTRIAL APPLICABILITY

As described and demonstrated above, the present invention provides a liposome aqueous suspension which is stable for a long period of time and undergoes no hydrolysis to form lyso-phospholipids even when preserved at a high temperature.

What is claimed is:

1. A liposome aqueous suspension containing taurine in the liposomes and the external aqueous phase, which contains 0.5 to 5.0% by weight of taurine based on the total amount of the liposome preparation and 0.05 to 20 mol %, based on the membrane component of the liposomes, of benzalkonium chloride in the membranes of the liposomes and the external aqueous phase.

* * * * *